:::

(12) United States Patent  
Southern, Jr.

(10) Patent No.: US 6,712,797 B1
(45) Date of Patent: Mar. 30, 2004

(54) BLOOD RETURN CATHETER

(75) Inventor: Lincoln Lee Southern, Jr., Denham Springs, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 42 days.

(21) Appl. No.: 09/664,658

(22) Filed: Sep. 19, 2000

(51) Int. Cl.[7] .................................. A61M 5/00
(52) U.S. Cl. ..................................... 604/264
(58) Field of Search .................. 604/6.05, 6.06, 604/6.1, 6.11, 6.16, 506, 507, 510, 35, 264

(56) References Cited

U.S. PATENT DOCUMENTS

| 217,711 A | | 7/1879 | Shiland | |
|---|---|---|---|---|
| 3,610,226 A | * | 10/1971 | Albisser | 128/2 |
| 4,551,292 A | | 11/1985 | Fletcher et al. | 264/139 |
| 4,617,019 A | | 10/1986 | Fecht et al. | 604/280 |
| 4,886,506 A | | 12/1989 | Lovgren et al. | 604/280 |
| 5,057,082 A | * | 10/1991 | Burchette, Jr. | 604/164 |
| 5,084,010 A | * | 1/1992 | Plaia et al. | 604/22 |
| 5,160,559 A | | 11/1992 | Scovil et al. | 156/73.6 |
| 5,501,674 A | * | 3/1996 | Trombley et al. | 604/247 |
| 5,507,299 A | * | 4/1996 | Roland | 600/575 |
| 5,509,910 A | | 4/1996 | Lunn | 604/282 |
| 5,531,673 A | | 7/1996 | Helenowski | 604/9 |
| 5,743,871 A | | 4/1998 | Strukel et al. | 604/35 |
| 5,800,409 A | | 9/1998 | Bruce | 604/280 |
| 5,833,670 A | * | 11/1998 | Dillon et al. | 128/919 |
| 5,873,864 A | * | 2/1999 | Luther et al. | 604/280 |
| 5,935,056 A | | 8/1999 | Kerin et al. | 600/114 |
| 5,938,645 A | * | 8/1999 | Gordon | 604/171 |
| 5,968,022 A | * | 10/1999 | Saito | 604/272 |
| 6,080,170 A | * | 6/2000 | Nash et al. | 606/159 |
| 6,165,157 A | * | 12/2000 | Dillon et al. | 128/919 |
| 6,210,375 B1 | * | 4/2001 | Moulton et al. | 604/195 |
| 6,213,978 B1 | * | 4/2001 | Voyten | 604/164.01 |

FOREIGN PATENT DOCUMENTS

JP  WO 97/37699  * 10/1997  .......... A61M/3/00

* cited by examiner

*Primary Examiner*—William E. Tapolcai
*Assistant Examiner*—Mohammad M. Ali
(74) *Attorney, Agent, or Firm*—André J. Porter; John H. Runnels; Bonnie J. Davis

(57) ABSTRACT

A blood vessel catheter with a non-planar tip that prevents or inhibits the catheter from adhering to the blood vessel wall or a blood clot when negative pressure is applied to the catheter to withdraw blood. The non-planar tip maintains its shape while in the blood vessel, while allowing blood to flow into the catheter.

6 Claims, 4 Drawing Sheets

14    22

14

22

BLOOD RETURN CATHETER

This invention relates to a catheter whose structure enables sampling of blood by decreasing the potential for adherence of the catheter tip to a blood vessel wall or a blood clot.

Catheters are sterilized or sterilizable, hollow tubes that may be placed in a blood vessel to allow continual access to the blood without having to re-puncture the patient. Blood catheters are used to collect blood or administer medications over time. However, a recurring problem in catheters used to collect blood samples is that the catheter tip can become blocked when negative pressure is applied to draw blood. When blockage of the catheter occurs, the patient must be re-punctured to collect a new blood sample. The primary cause of blockage is adherence of the catheter tip to the sides of the vessel walls, thus preventing the return of blood flow. An additional cause of blockage is a blood clot that blocks the catheter tip.

An unfilled need exists for a catheter that decreases the chance of blockage when applying negative pressure during blood sampling.

U.S. Pat. No. 5,935,056 describes a device for viewing a region of a fallopian tube, comprising an optical viewing scope and an access catheter having a distal spacing structure which facilitates separation of the tubal wall of the fallopian tube from the optical viewing scope.

U.S. Pat. No. 5,531,673 describes a tubular ventricular catheter that prevents clogging, and reduces the tearing of brain tissue when the proximal tip of the device is withdrawn from the brain cavity. The catheter has a rounded open end and two longitudinal slots cut in the side wall of the proximal end. The longitudinal slots are scalloped by semi-circular cut-outs.

U.S. Pat. No. 5,509,910 describes a multi-part catheter which comprises a high strength bond between a tubular shaft and a more flexible distal tip by employing a high tensile strength transition segment.

U.S. Pat. No. 4,886,506 describes a catheter tube with improved torque control and a tapered end that allows a more secure connection to a soft tip.

U.S. Pat. No. 5,160,559 describes a guide catheter having a high strength, lap-joint tip bond, comprising two shaft members linked by a high surface area connection. The first shaft member is composed of a soft, deformable tubular tip, while the second shaft member is composed of a thermoplastic, tubular member.

U.S. Pat. No. 4,617,019 describes a method for cutting a catheter at an acute angle to reduce undesirable protuberances when the catheter is flattened for insertion.

U.S. Pat. No. 4,551,292 describes a process for fabricating a catheter having a soft, deformable, bulbous tip composed of a thermoplastic or elastomeric material.

U.S. Pat. No. 217,711 describes a urethra catheter with a "duck-bill or V-shaped" tip with elastic branches that compress to a wedge shape when the catheter enters and follows the canal of the urethra. Upon entering the bladder, the elastic branches of the V-shaped tip reopen to allow sampling of the bladder fluid.

None of these prior devices address the need for a catheter that reduces or eliminates blockage of a catheter when negative pressure is applied. An unfilled need exists for a catheter that avoids adherence to a blood vessel wall or to a blood clot.

I have discovered a catheter and a method that decreases the blockage problem while collecting blood. The device is a sterilized or sterilizable catheter with a non-planar tip. To avoid adherence to the blood vessel wall, the catheter tip is shaped, by either cutting or molding, in a way that makes the terminal end sufficiently non-planar to inhibit or prevent the formation of a seal with a blood vessel wall. The non-planar shape can, for example, be a V-shape tip whose branches are sufficiently short to maintain the catheter's shape and to prevent closing by blood vessel wall pressure. In alternative embodiments, the non-planar tip can be serrated, castellated, or cut in an undulated manner. The tip should allow the passage of blood when the terminal end of the catheter is against a blood vessel wall, while maintaining sufficient strength to inhibit or prevent the expansion or collapse of the tip.

The novel catheter avoids adhering to a blood vessel wall when a negative pressure is applied to withdraw blood. The catheter allows blood sampling with little to no blockage. The catheter can be initially sterilized by the manufacturer, or sterilized by the end user before use. If the terminal end of the catheter becomes lodged against the blood vessel wall, blood flow is maintained because the non-planar shape of the catheter tip prevents total blockage since its shape does not allow it to form a seal with a blood vessel wall. Thus, re-catheterizing a patient is prevented or greatly reduced.

As used in the specification and claims, a "non-planar tip" of a catheter means a tip whose exposed or cut surface does not lie in a plane, and that departs sufficiently from a planar shape. When used as a portion of a catheter in a blood vessel, and ordinary negative pressure is applied to withdraw blood, the tip adheres to the blood vessel wall about 2% of the time or less.

Figure 1:
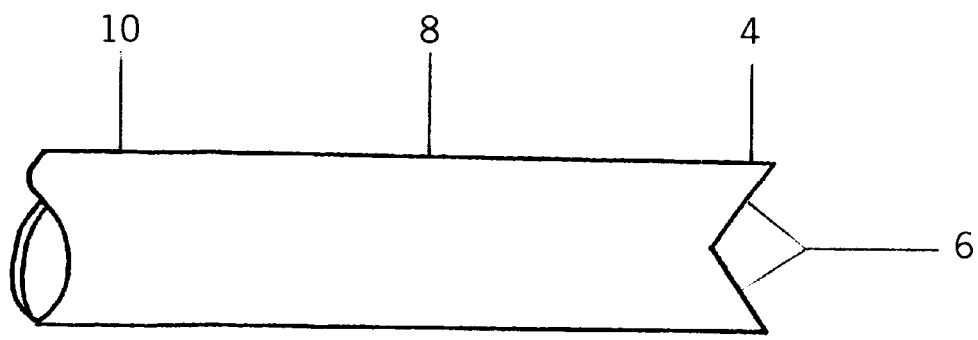
FIG. 1 illustrates a side view of one embodiment of a blood vessel catheter with a V-shape tip.
Figure 2:
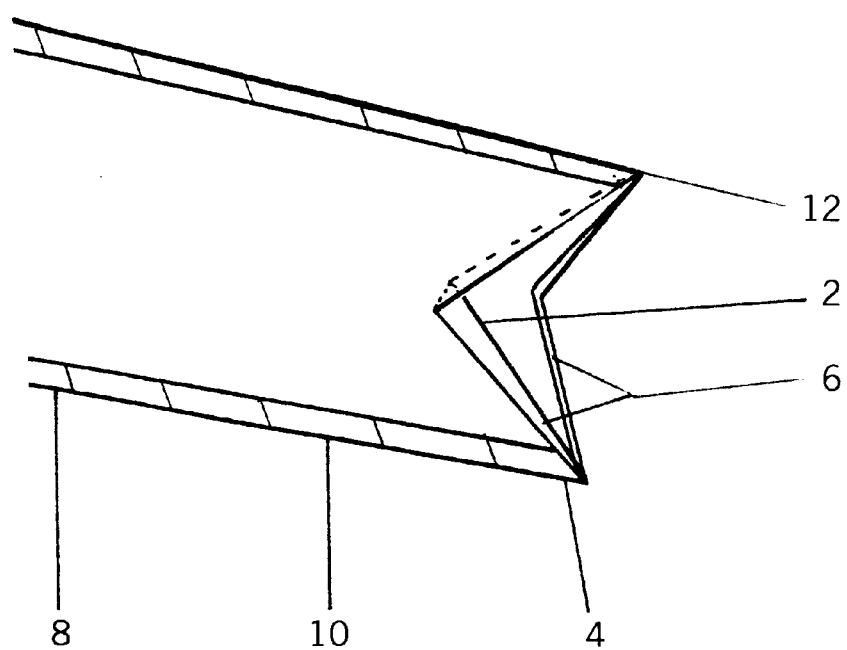
FIG. 2 illustrates a cross-sectional, perspective view of the blood vessel catheter of FIG. 1 with a V-shape tip.

FIGS. 1 and 2 illustrate one embodiment of the catheter with a V-shape tip. This embodiment comprises a V-shape tip 12, a lumen 2 and branches 6. The branches 6 extend from the proximal end 10 to the distal end 4 of the flexible tubular shaft 8. The branches 6 have a length sufficient to create and maintain spacing between the lumen 2 and a blood vessel wall, but short enough to resist closure during transport through a blood vessel. The spacing created by the branches 6 prevents blockage of the lumen 2 when taking a blood sample. One method to achieve a V-shape tip is to cut a standard catheter tip by cutting two diagonals toward the center of the catheter. The tip of the catheter 8 can be modified and sterilized by a manufacturer prior to packaging or by medical personnel prior to use.

Figure 3:
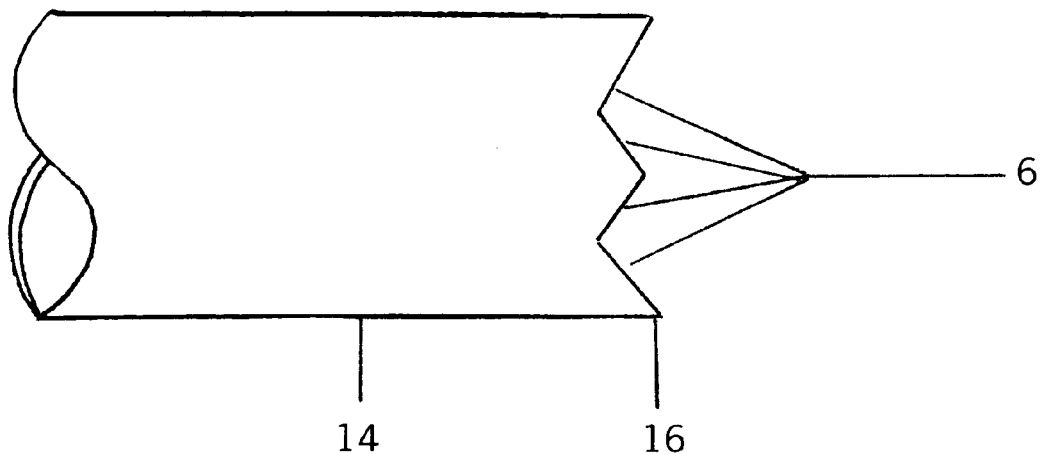
FIG. 3 illustrates a side view of one embodiment of a blood vessel catheter with a serrated tip.
Figure 4:
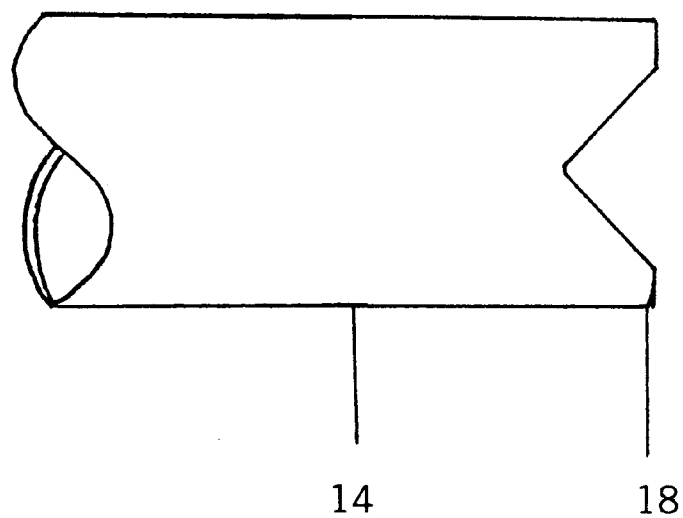
FIG. 4 illustrates a cross sectional side view of one embodiment of a blood vessel catheter with a V-shape tip, having ends that are flat instead of pointed.
Figure 5A:
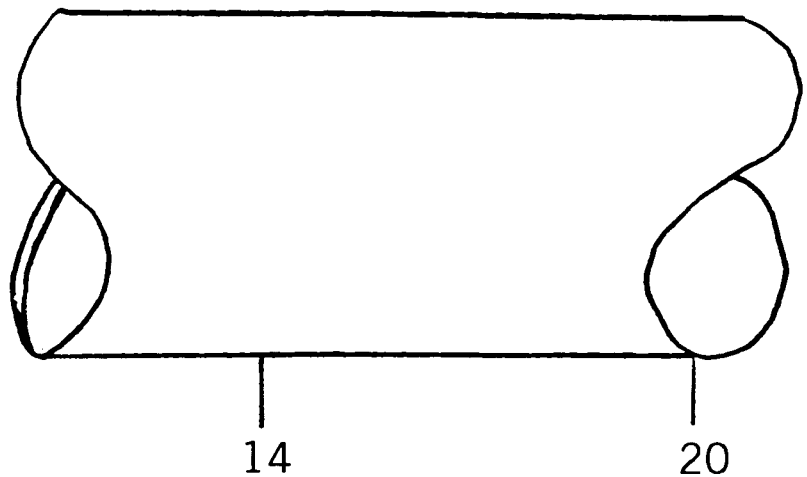
FIGS. 5A and 5B illustrate a perspective view and a side view, respectively, of one embodiment of a blood vessel catheter with an undulated tip.
Figure 5B:
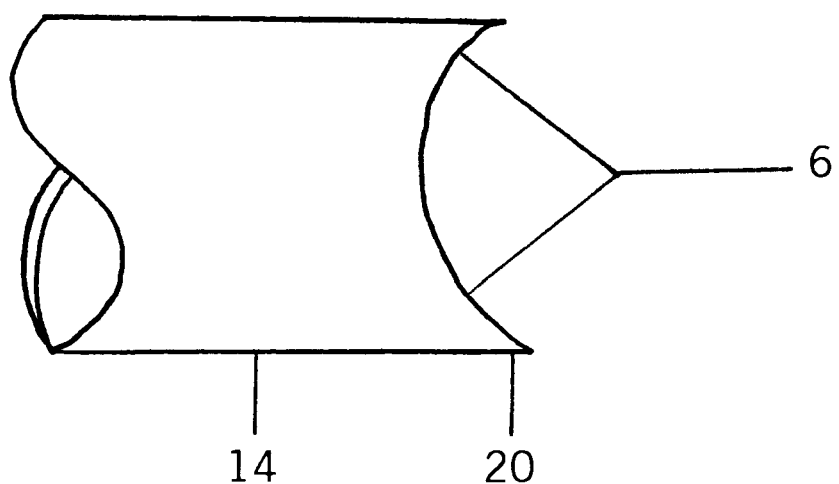
Figure 6A:
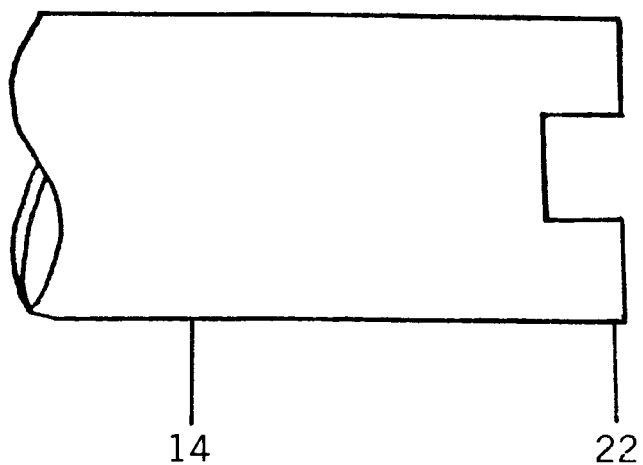
FIGS. 6A and 6B illustrate a side view and a perspective view, respectively, of one embodiment of a blood vessel catheter with a castellated tip.
Figure 6B:
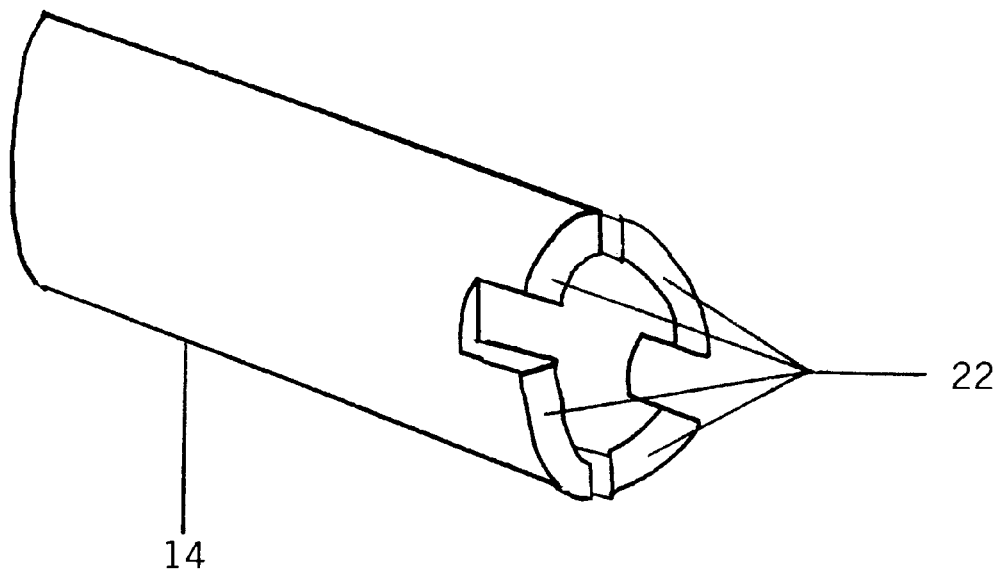

FIGS. 3–6 illustrate other embodiments of a non-planar tip 12. FIG. 3 illustrates a catheter 14 having a serrated shape tip 16. FIG. 4 illustrates a catheter having a V-shape tip with flat ends 18. FIGS. 5A and 5B illustrate a catheter 14 having an undulated tip 20. FIG. 5A illustrates a perspective view of the undulated tip 20, and FIG. 5B illustrates a side view of the tip 20. FIGS. 6A and 6B illustrate a catheter 14 having a castellated tip 22. FIG. 6A illustrates a side view of the castellated tip 22, and FIG. 6B illustrates a perspective view of the tip 22.

EXAMPLE 1

Glucose tolerance experiments involving catheters composed of Tygon® tubing were conducted by sampling the blood of over one hundred pigs. Tests were performed using catheters having planar and non-planar tips. The non-planar tip catheters comprised catheter tips cut in a V-shape with an angle of approximately 90 degrees between each branch. Each experiment lasted from 3 to 10 days, during which time blood was withdrawn at various cycles of 5, 15 and 30 minutes, lasting for time periods of 30, 60 and 120 minutes. When using a planar tip catheter, 25–50% of the catheters would close before the end of the experiment. The pigs had to be re-catheterized. However, when using the V-shaped embodiment of the non-planar tip, none of the catheters became blocked.

The complete disclosures of all references cited in this specification are hereby incorporated by reference. In the event of an otherwise irreconcilable conflict, however, the present specification shall control.

I claim:

1. A method for withdrawing blood from a patient's blood vessel; said method comprising inserting into the blood vessel a flexible catheter, and applying negative pressure to the catheter to cause the withdrawal of blood; wherein the catheter comprises a non-planar tip selected from the group consisting of V-shaped tips, serrated tips, and castellated tips; wherein the tip resists adhesion to a blood vessel wall or to a blood clot when negative pressure is applied to the catheter, and wherein the tip is sufficiently rigid to maintain its shape without substantial collapse when the tip is inserted into the blood vessel; wherein blood is withdrawn from the blood vessel without the tip's adhering to a blood vessel wall or to a blood clot.

2. A method as recited in claim 1, wherein the tip is a V-shaped tip.

3. A method as recited in claim 1, wherein the tip is a serrated tip.

4. A method as recited in claim 1, wherein the tip is a castellated tip.

5. A flexible catheter for withdrawing blood from a blood vessel, wherein said catheter comprises a non-planar tip selected from the group consisting of V-shaped tips, serrated tips, and castellated tips; wherein the tip resists adhesion to a blood vessel wall or to a blood clot when negative pressure is applied the catheter to withdraw blood from within a blood vessel, and wherein said tip is sufficiently rigid to maintain its shape without substantial collapse when said tip is inserted into a blood vessel.

6. A flexible catheter as recited in claim 5, wherein said tip is a castellated tip.

* * * * *